United States Patent
Cai et al.

(10) Patent No.: US 10,920,259 B2
(45) Date of Patent: Feb. 16, 2021

(54) TWO ELECTRODES FUNCTIONING AS THREE ELECTRODES IN THE FLUID CHAMBER OF A TEST STRIP

(71) Applicant: Sinocare Inc., Changsha (CN)

(72) Inventors: Xiaohua Cai, Changsha (CN); Liang Shen, Changsha (CN); Limingxuan Xu, Changsha (CN); Pengshu Wang, Changsha (CN); Qiang Zou, Changsha (CN); Chen Xiao, Changsha (CN); Yuehui Li, Changsha (CN)

(73) Assignee: Changsha Sinocare Inc., Changsha (CN)

( * ) Notice: Subject to any disclaimer, the term of this patent is extended or adjusted under 35 U.S.C. 154(b) by 94 days.

(21) Appl. No.: 16/263,664

(22) Filed: Jan. 31, 2019

(65) Prior Publication Data
US 2020/0157596 A1   May 21, 2020

(30) Foreign Application Priority Data

Nov. 20, 2018   (CN) .......................... 2018 1 1382916

(51) Int. Cl.
 *C12Q 1/00* (2006.01)
 *A61B 5/145* (2006.01)
 *G01N 27/327* (2006.01)

(52) U.S. Cl.
 CPC .......... *C12Q 1/006* (2013.01); *A61B 5/14532* (2013.01); *G01N 27/3271* (2013.01)

(58) Field of Classification Search
 CPC ... C12Q 1/006; A61B 5/14532; A61B 5/1486; A61B 2562/0295; G01N 27/3271; G01N 27/3272; G01N 27/3274
 See application file for complete search history.

(56) References Cited

U.S. PATENT DOCUMENTS

| | | | | |
|---|---|---|---|---|
| 5,243,516 A | * | 9/1993 | White | G01N 27/3273 204/401 |
| 6,475,372 B1 | * | 11/2002 | Ohara | G01N 27/3274 204/406 |
| 8,815,076 B2 | * | 8/2014 | Cardosi | G01N 27/3274 205/777.5 |
| 2005/0139469 A1 | | 6/2005 | Davies et al. | |
| 2005/0176153 A1 | * | 8/2005 | O'hara | G01N 27/3274 436/70 |
| 2010/0270178 A1 | * | 10/2010 | Guo | A61B 5/1486 205/777.5 |

(Continued)

FOREIGN PATENT DOCUMENTS

CN   106353387 A   1/2017

*Primary Examiner* — Maris R Kessel
*Assistant Examiner* — Joshua L Allen
(74) *Attorney, Agent, or Firm* — Lambert Shorten & Connaughton; David J. Connaughton, Jr.; Gary E. Lambert

(57) ABSTRACT

An improved disposable electrochemical test sensor designed to facilitate reducing volume of fluid samples. It has a short fluid chamber having two electrodes that functions as three electrodes (one working electrode, one reference electrode and one blank electrode). The chamber provides a reservoir from which a sample fluid can be quickly drawn into the chamber through capillary action. The novel potential reverse and curve-fitting technology of the test sensor provided by the present invention can effectively eliminate most common interferents existing in the fluid samples.

17 Claims, 8 Drawing Sheets

(56) References Cited

U.S. PATENT DOCUMENTS

| | | | |
|---|---|---|---|
| 2011/0155584 A1* | 6/2011 | Chatelier | G01N 33/49 205/777.5 |
| 2015/0377825 A1* | 12/2015 | Tsai | G01N 27/3274 205/782 |
| 2016/0320331 A1* | 11/2016 | Chuang | G01N 27/3274 |
| 2017/0240945 A1* | 8/2017 | Marquant | G01N 27/3274 |

* cited by examiner

Table 1: Test results before background correction

| Interference | Interference concentration | Unspiked/Spiked | Glucose Reading | % Bias |
|---|---|---|---|---|
| Acetoaminophen | 20 mg/dL | Unspiked | 5.80 | 12.6% |
| | | Spiked | 6.53 | |
| | | Unspiked | 15.61 | 12.7% |
| | | Spiked | 17.59 | |
| Methyldopa | 20 mg/dL | Unspiked | 4.68 | 33.4% |
| | | Spiked | 6.25 | |
| | | Unspiked | 15.10 | 10.9% |
| | | Spiked | 16.75 | |
| Vitamine C | 3 mg/dL | Unspiked | 6.77 | 6.1% |
| | | Spiked | 7.18 | |
| | | Unspiked | 14.92 | 3.7% |
| | | Spiked | 15.47 | |
| Glutathione | 92 mg/dL | Unspiked | 4.79 | 30.3% |
| | | Spiked | 6.23 | |
| | | Unspiked | 14.67 | 12.6% |
| | | Spiked | 16.52 | |
| L-Dopa | 20 mg/dL | Unspiked | 4.51 | 37.0% |
| | | Spiked | 6.17 | |
| | | Unspiked | 14.51 | 10.6% |
| | | Spiked | 16.05 | |
| Bilirubin | 50 mg/dL | Unspiked | 5.14 | 13.9% |
| | | Spiked | 5.86 | |
| | | Unspiked | 15.98 | 3.9% |
| | | Spiked | 16.60 | |
| Uric acid | 24 mg/dL | Unspiked | 4.85 | 26.5% |
| | | Spiked | 6.14 | |
| | | Unspiked | 15.28 | 12.9% |
| | | Spiked | 17.25 | |

Fig. 6

Table 2: Test results after background correction

| Interference | Interference concentration | Unspiked/Spiked | Glucose Reading | % Bias |
|---|---|---|---|---|
| Acetoaminophen | 20 mg/dL | Unspiked | 5.80 | -2.4% |
| | | Spiked | 5.66 | |
| | | Unspiked | 15.61 | 5.3% |
| | | Spiked | 16.44 | |
| Methyldopa | 20 mg/dL | Unspiked | 4.68 | 1.7% |
| | | Spiked | 4.76 | |
| | | Unspiked | 15.10 | 5.5% |
| | | Spiked | 15.93 | |
| Vitamine C | 3 mg/dL | Unspiked | 6.77 | 4.3% |
| | | Spiked | 7.06 | |
| | | Unspiked | 14.92 | 3.3% |
| | | Spiked | 15.41 | |
| Glutathione | 92 mg/dL | Unspiked | 4.79 | 0.5% |
| | | Spiked | 4.81 | |
| | | Unspiked | 14.67 | 3.0% |
| | | Spiked | 15.12 | |
| L-Dopa | 20 mg/dL | Unspiked | 4.51 | 7.9% |
| | | Spiked | 4.86 | |
| | | Unspiked | 14.51 | 2.0% |
| | | Spiked | 14.80 | |
| Bilirubin | 50 mg/dL | Unspiked | 5.14 | 3.2% |
| | | Spiked | 5.30 | |
| | | Unspiked | 15.98 | -2.8% |
| | | Spiked | 15.53 | |
| Uric acid | 24 mg/dL | Unspiked | 4.85 | 6.0% |
| | | Spiked | 5.14 | |
| | | Unspiked | 15.28 | 6.5% |
| | | Spiked | 16.27 | |

Fig. 7

TWO ELECTRODES FUNCTIONING AS THREE ELECTRODES IN THE FLUID CHAMBER OF A TEST STRIP

FIELD OF THE INVENTION

The present invention generally relates to a test sensor or strip. More specifically, the present invention generally relates to a disposable biosensor with a thin layer fluid chamber that is adapted to receive a fluid sample with small volume. Still more specifically, the present invention generally relates to an electrochemical biosensor with a short fluid chamber that requires less fluid sample. Still more specifically, the present invention generally relates an electrochemical biosensor with the fluid chamber containing only two electrodes that function as three electrodes. Still more specifically, the present invention relates to methods of making and using the biosensors.

BACKGROUND OF THE INVENTION

Electrochemical biosensors or disposable test sensors such as glucose strips are well known and have been used to determine the concentration of various analytes from biological samples, particularly from blood. The accurate determination of analytes in body fluids is of great importance in the diagnoses of certain physiological abnormalities. In particular, it is important that diabetic individuals frequently check their glucose level in their body fluids to regulate the glucose intake in their daily diets. The results of such tests can be used to determine the insulin dosage or other medication needs to be administered. In one type of blood-glucose testing system, test sensors, often called glucose strips, are used by diabetic individuals to test a sample of blood in connection with a hand-held meter. The glucose strips are used by millions of diabetics throughout the world on a daily basis.

There are hundreds of brand names of glucose strips in the market. They are very similar in terms of sensor construction: i.e., a channel or chamber is formed between a generally U-shaped spacer and is adapted to receive blood from the opening end of the sensor through capillary action and escape air from the other end through an air escape vent. It is well known that blood sample contains various endogenous and exogenous compounds that may produce current signals, i.e, background current signals, thus, interfere with the testing of analytes, because the background current signals are added up to the analyte (e.g. glucose) signal. Therefore, in order to eliminate the interference, the fluid chamber of the test sensor normally contains three electrodes in the prior arts: one working electrode that is loaded with an enzyme, a mediator, a stabilizer and other ingredients; one reference electrode that is loaded with similar chemistry as the working electrode; and one blank electrode that is loaded with the same chemistry as the working electrode except without adding the enzyme. A potential (for example, 0.4V vs the reference electrode) is applied to the working electrode and the blank electrode at the same time for a certain time, for example, 5 s. The current signal at the working electrode represents signals not only both from the analyte (e.g. glucose) but also from various interferents such as vitamin C, acetaminophen and others, while the current signal at the blank electrode represents from various interferents such as vitamin C, acetaminophen and others. So, by subtracting the black background current signal from the working electrode signal, one can obtain a current signal related to the analyte (e.g. glucose) concentration, thus eliminate the interference from co-existing interferents such as vitamin C, acetaminophen and others.

In order to reduce blood volume, thus reduce pain from piercing finger, the blood receiving chamber should be as small and as possible. Therefore, it would be highly desirable to have a small chamber that requires less blood volume while there is still no compromise of performance of the test sensor. One can imagine the chamber volume can be reduced by either reducing length, width, or thickness of the chamber, or combination thereof. However, there are some limitations by reducing the width. If the width is too narrow, the patients or users cannot easily locate the opening end because many users have vision problems or trembling hands. Reducing the thickness of the chamber is also troublesome, this makes the capillary action less effective, thus resulting in insufficient or non-continuous filling. All of these may cause inaccurate test results. The present disclosure focuses on reducing the chamber length by directing to a novel design and method to overcome one or more of the limitations in the prior arts.

SUMMARY OF THE INVENTION

According to the first embodiment, a disposable electrochemical test sensor has a fluid sample chamber having two electrodes that function as three electrodes. Such a design is adapted to reduce the volume of fluid samples. The fluid chamber provides a reservoir from which sample fluid can be drawn into the sample receiving chamber through capillary action. In preferred embodiments, the sensor consists of multiple layers which include a first base layer having conductive coatings serving as working electrode, reference or/and blank electrode; a second base layer being adhesive tape or insulating printing, having two cutouts or exposed areas to define the electrode areas and load or confine chemistries; a first upper layer having semi-circular or U-shape cutout serving as spacer; and a second upper layer with a hydrophilic surface facing to the chamber and vent openings at the distal end of the chamber. The base and upper layers are attached through adhesives or other ways to bond each other. Note that the two base layers and the second upper layer are aligned at the front end. As such, the fluid chamber is formed between a portion of the lower layer surface and the upper layer surface at one end of the sensor, while the other end of the sensor having conductive layer exposed serve as electric contacts in connection with a monitor or meter. As used herein, the term "meter" is used to generally refer to monitors, meters, and instruments that can receive test strips and provide an output relating to an analyte. Typically, meters have computerized elements such as a processor, memory, and/or display which can carry out various functions performed by the meter.

The first electrode which is close to the sampling entrance, serving as either blank or reference electrode, is loaded with a chemistry containing at least a mediator, a stabilizer, a binder and other ingredients. The second electrode which is located at the other end of the chamber close to the vent opening, serving as either reference or working electrode, is loaded with same chemistry as the first electrode, but, with addition of an enzyme, such as glucose oxidase, glucose dehydrogenase, that can react with the analyte (glucose). Assuming a test time of 5 s, a potential (e.g., 0.4V) is applied to the first electrode against the second electrode (i.e. 0V potential at this electrode) for a short time, preferably for 1 s, more preferably, for 2 s, and the current at the first electrode is recorded for each time point, e.g. each 100 ms. Following the first 2 s, a short period of pause, 100 ms for example, the potential application is reversed: the same potential (e.g., 0.4V) is applied to the second electrode against the first electrode (i.e. 0V potential at this electrode) for another 3 s, this makes the total test time around 5 s. The current at the second electrode represents working electrode signal that is mainly related to the analyte concentration. In general, the current at 5 s is used for the analyte concentration calculation. Since there is no enzyme at the first electrode, thus, the current at the first electrode represents background current signal. Note that the current signals are recorded up to 2 s only and are not equivalent to the background current at 5 s. To mimic the background current at 5 s time point, the data points recorded at the first electrode from the very first time point (e.g. 0.1 s) to 2 s are curve-fitted in order to extrapolate the current values up to 5 s. The resulting current—time equation can be used to calculate the background current at 5 s. This potential reverse and curve-fitting technology enable the test sensor having a shorter fluid chamber with two electrodes only to function as three electrodes (i.e., one blank electrode, one reference electrode and one working electrode). There is no doubt that the fluid chamber with two electrodes can be shorter than that with three electrodes, thus, and the chamber volume is significantly reduced.

According to the second embodiment, a disposable electrochemical test sensor has a fluid sample chamber having two electrodes that function as three electrodes. Such a design is adapted to reduce the volume of fluid samples. The fluid chamber provides a reservoir from which sample fluid can be drawn into the sample receiving chamber through capillary action. In preferred embodiments, the sensor consists of multiple layers which include a first base layer having conductive coatings serving as working electrode and reference or blank electrode; a second base layer being adhesive tape or insulating printing, having two cutouts or exposed areas to define the electrode areas and load chemistries; a first upper layer having semi-circular or U-shape cutout serving as spacer; and a second upper layer with a hydrophilic surface facing to the chamber and vent openings at the distal end of the chamber. The base and upper layers are attached through adhesives or other ways to bond each other. Note that the two base layers and the second upper layer are aligned at the front end. As such, the fluid chamber is formed between a portion of the lower layer surface and the upper layer surface at one end of the sensor, while the other end of the sensor having conductive layer exposed serve as electric contacts in connection with a monitor or meter.

The first electrode which is close to the sampling entrance, serving as either reference electrode or working electrode, is loaded with a chemistry containing at least an enzyme, such as glucose oxidase, glucose dehydrogenase, that can react with the analyte (glucose), a mediator, a stabilizer, a binder and other ingredients. The second electrode which is located at the other end of the chamber close to the vent opening, serving as either blank electrode or reference electrode, is loaded with same chemistry as the first electrode, but, without addition of the enzyme. Assuming a test time of 5 s, a potential (e.g., 0.4V) is applied to the second electrode against the first electrode (i.e. 0V potential at this electrode) for a short time, preferably for 1 s, more preferably, for 2 s, and the current at the second electrode is recorded for each time point, e.g. each 100 ms. Following the first 2 s, a short period of pause, 100 ms for example, the potential application is reversed: the same potential (e.g., 0.4V) is applied to the first electrode against the second electrode (i.e. 0V potential at this electrode) for another 3 s, this makes the total test time around 5 s. The current at the first electrode represents working electrode signal that is mainly related to the analyte concentration. In general, the current at 5 s is used for the analyte concentration calculation. Since there is no enzyme at the second electrode, thus, the current at the second electrode represents background current signal. Note that the current signals are recorded up to 2 s only and are not equivalent to the background current at 5 s. To mimic the background current at 5 s time point, the data points recorded at the second electrode from the very first time point (e.g. 0.1 s) to 2 s are curve-fitted in order to extrapolate the current values up to 5 s. The resulting current—time equation can be used to calculate the background current at 5 s. This potential reverse and curve-fitting technology enable the test sensor having a shorter fluid chamber with two electrodes only to function as three electrodes (i.e., one blank electrode, one reference electrode and one working electrode). There is no doubt that the fluid chamber with two electrodes can be shorter than that with three electrodes, thus, and the chamber volume is significantly reduced.

BRIEF DESCRIPTION OF THE DRAWINGS

FIG. 6 summarizes test results before background correction.

FIG. 7 summarizes test results after background correction.

DETAILED DESCRIPTION OF ILLUSTRATED EMBODIMENTS

The test sensor of the present invention is directed to reduce sample volume for the determination of an analyte concentration of in a fluid sample, such as blood. In one embodiment, a test sensor is adapted to receive a fluid sample from one end of the sensor, while the other end is connected with an instrument or meter. Analytes that may be measured include, but are not limited to glucose, lactate, uric acid, β-hydroxybutyric acid, creatinine, creatine, cholesterol, triglycerides, hemoglobin, bilirubin, alcohol, etc. The fluid sample may be any body fluid, thus, the analytes may be in, for example, a whole blood sample, a blood serum sample, a blood plasma sample, other body fluids like tears, interstitial fluid and urine. In one preferred method, the testing equipment is a hand-held meter.

In one embodiment, a disposable electrochemical test sensor has a fluid sample chamber having two electrodes that function as three electrodes. Such a design is adapted to reduce the volume of fluid samples. The fluid chamber provides a reservoir from which sample fluid can be drawn into the sample receiving chamber through capillary action. In preferred embodiments, the sensor consists of multiple layers which include a first base layer having conductive coatings serving as working electrode and reference or blank electrode; a second base layer being adhesive tape or insulating printing, having two cutouts or exposed areas to define the electrode areas and load chemistries; a first upper layer having semi-circular or U-shape cutout serving as spacer; and a second upper layer with a hydrophilic surface facing to the chamber and vent openings at the distal end of the chamber. The base and upper layers are attached through adhesives or other ways to bond each other. Note that the two base layers and the second upper layer are aligned at the front end. As such, the fluid chamber is formed between a portion of the lower layer surface and the upper layer surface at one end of the sensor, while the other end of the sensor having conductive layer exposed serve as electric contacts in connection with a monitor or meter. For the sensor chamber of the present invention, the electric contact end at the other end of the sensor need only two contacts used for one working electrode and one reference electrode, respectively.

Figure 1A:
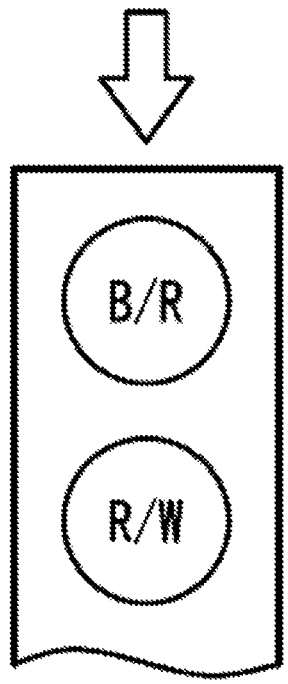
FIG. 1A is a perspective graph showing a fluid chamber of the test sensors that has two electrodes (B/R and R/W). Arrow denotes sampling direction.

FIG. 1A is a perspective view of the fluid chamber of the test sensors of the present invention according to the first embodiment. The chamber has two electrode areas, B/R and R/W. The first electrode (B/R) which is close to the sampling entrance, serving as either blank or reference electrode, is loaded with a chemistry containing at least a mediator such as potassium ferricyanide, potassium ferrocyanide and so on, a stabilizer, a binder and other ingredients. The second electrode (R/W) which is located at the other end of the chamber close to the vent opening, serving as either reference electrode or working electrode, is loaded with same chemistry as the first electrode, but with addition of an enzyme such as glucose oxidase, glucose dehydrogenase that can react with the analyte (glucose). Assuming a test time of 5 s, a potential (e.g., 0.4V) is applied to the first electrode against the second electrode (i.e. keeping 0V at this electrode) for the first 1 s, preferably, for the first 2 s. In this case, the first electrode actually functions as a blank electrode, while the second electrode functions as a reference electrode. Since there is no enzyme loaded at the first electrode, thus, the current at the first electrode represents background current signal. The current at the first electrode is recorded for each time point, e.g. each 100 ms. Following the first 2 s, a short period of pause (100 ms for example) is applied in order to reverse the potential application in the next step. The same potential (e.g., 0.4V) is now applied to the second electrode against the first electrode (i.e. keeping 0V at this electrode) for the last 3 s. In this case, the first electrode actually functions as a reference electrode, while the second electrode functions as a working electrode which is loaded with an enzyme. The current at the second electrode is recorded for each time point, e.g. each 100 ms, which represents working electrode signal related to the analyte concentration.

In general, the current at the working electrode at 5 s time point is used for calculation. However, there is no corresponding background current at the same time point. To calculate the 5 s background current, the current data points recorded at the first electrode from the very first time point (e.g. 0.1 s) to 2 s are curve-fitted. The resulting current—time equation is used to calculate the background current at 5 s. A difference between the background current and working electrode current can be calculated, with the difference being a current signal representing an analyte concentration. In one embodiment, the background current at 5 s can be subtracted from the working electrode current at 5 s, and the resulting current thus represents the analyte signal and relates its concentration.

Figure 1B:
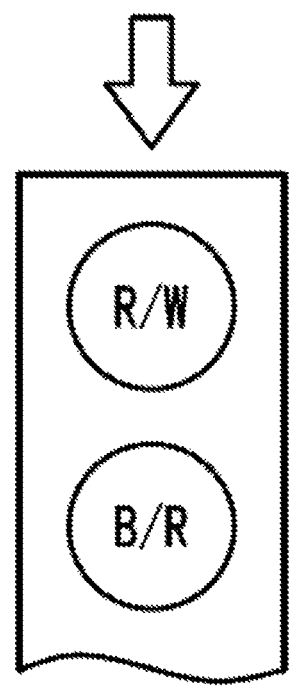
FIG. 1B is a perspective graph showing a fluid chamber of the test sensors that has two electrodes (R/W and B/R). Arrow denotes sampling direction.

FIG. 1B is a perspective view of the fluid chamber of the test sensors of the present invention according to the second embodiment. The chamber has two electrode areas R/W and B/R. The first electrode (R/W) which is close to the sampling entrance, serving as either reference electrode or working electrode, is loaded with a chemistry containing at least an enzyme such as glucose oxidase, glucose dehydrogenase that can react with the analyte (glucose), a mediator such as potassium ferricyanide, potassium ferrocyanide and so on, a stabilizer, a binder and other ingredients. The second electrode (B/R) which is located at the other end of the chamber close to the vent opening, serving as either blank electrode or reference electrode, is loaded with same chemistry as the first electrode, but without addition of an enzyme. Assuming a test time of 5 s, a potential (e.g., 0.4V) is applied to the second electrode against the first electrode (i.e. keeping 0V at this electrode) for the first 1 s, preferably, for the first 2 s. In this case, the second electrode actually functions as a blank electrode, while the first electrode functions as a reference electrode. Since there is no enzyme loaded at the second electrode, thus, the current at the second electrode represents background current signal. The current at the second electrode is recorded for each time point, e.g. each 100 ms. Following the first 2 s, a short period of pause (100 ms for example) is applied in order to reverse the potential application in the next step. The same potential (e.g., 0.4V) is now applied to the first electrode against the second electrode (i.e. keeping 0V at this electrode) for the last 3 s. In this case, the second electrode actually functions as a reference electrode, while the first electrode functions as a working electrode which is loaded with an enzyme. The current at the first electrode is recorded for each time point, e.g. each 100 ms, which represents working electrode signal related to the analyte concentration. This arrangement of R/W-B/R, i.e. a sample passes R/W electrode first, then B/R, may be beneficial for accurate test results in case of insufficient blood sample that does not fill up the fluid chamber (e.g. partially covers the second electrode.)

The above potential reverse and curve-fitting technology enable the test sensor to use two electrodes functioning as three electrodes (one blank electrode, one reference electrode and one working electrode). Thus, the chamber length is shorten and chamber volume is reduced.

Figure 2:
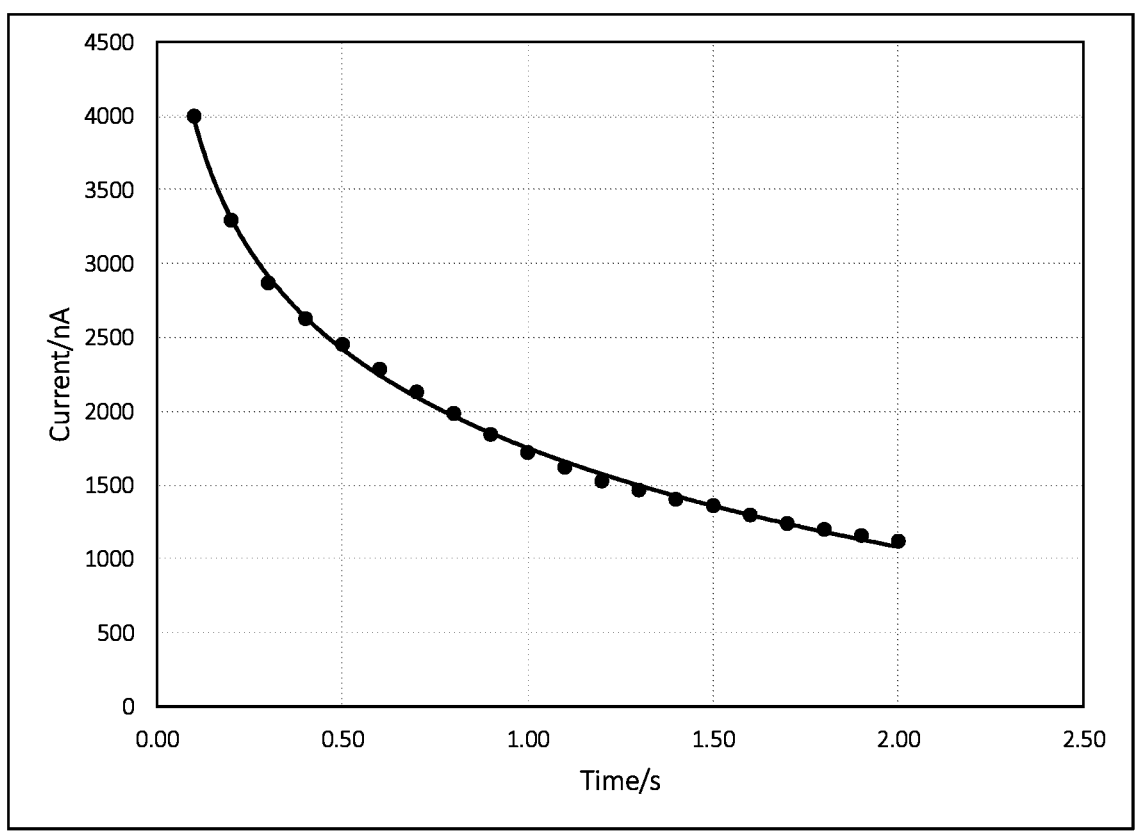
FIG. 2 is a typical current vs time (i-t) curve of background signal from 0.1 to 2 s.
Figure 3:
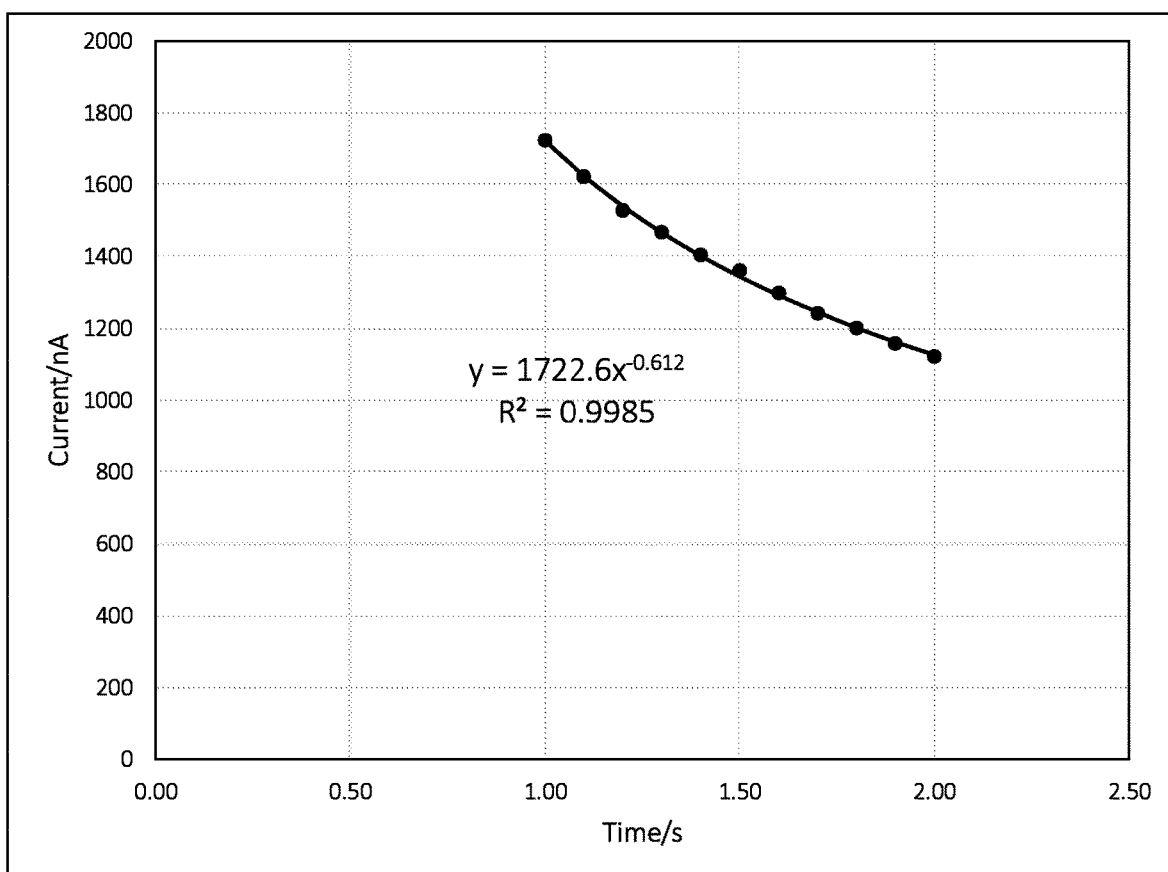
FIG. 3 is a current vs time (i-t) curve of background signal from 1 to 2 s. The equation and regression coefficient are derived from the data points of current vs time (1 to 2 s).

FIG. 2 is a typical current vs time (i-t) curve of background signal recorded every 0.1 s starting from 0.1 to 2 s. Higher currents at very early stage are due to charging current. It may be erratic and not reproducible. It may also cause a bad curve-fitting (low regression coefficient, less than 0.95 for example) and thus give wrong background current calculated from curve fitting equation assuming time point at 5 s. It has been found out that better curve-fitting (higher regression coefficient, larger than 0.95) can be obtained by ignoring the first a few data points. Preferably, the curve-fitting starts from 0.5 to 2 s. More preferably, the curve-fitting starts from 1 to 2 s. There are several curve-fitting methods, such as polynomial, exponential, logarithm and so on. It has been found out that the i-t curve in the electrochemical test sensor of the present invention is always a decaying curve. It seems an exponential curve-fitting turns out better results than other methods in terms of higher regression coefficient and thus used throughout this work. FIG. 3 is a current vs time (i-t) curve of background signal from 1 to 2 s. Also shown in the figure is curve-fitting equation:

$$y=ax^b \quad (1)$$

Where a in the equation (1) equals to 1722.6, b equals to −0.612, x and y in the equation represent time (s) and current (nA), respectively. A regression coefficient of 0.9985 is also derived from the given data points of current vs time (1 to 2 s), which shows a good curve-fitting. From the equation (1), one can easily figure out a current value at a given time, for example, 5 s.

Figure 4A:
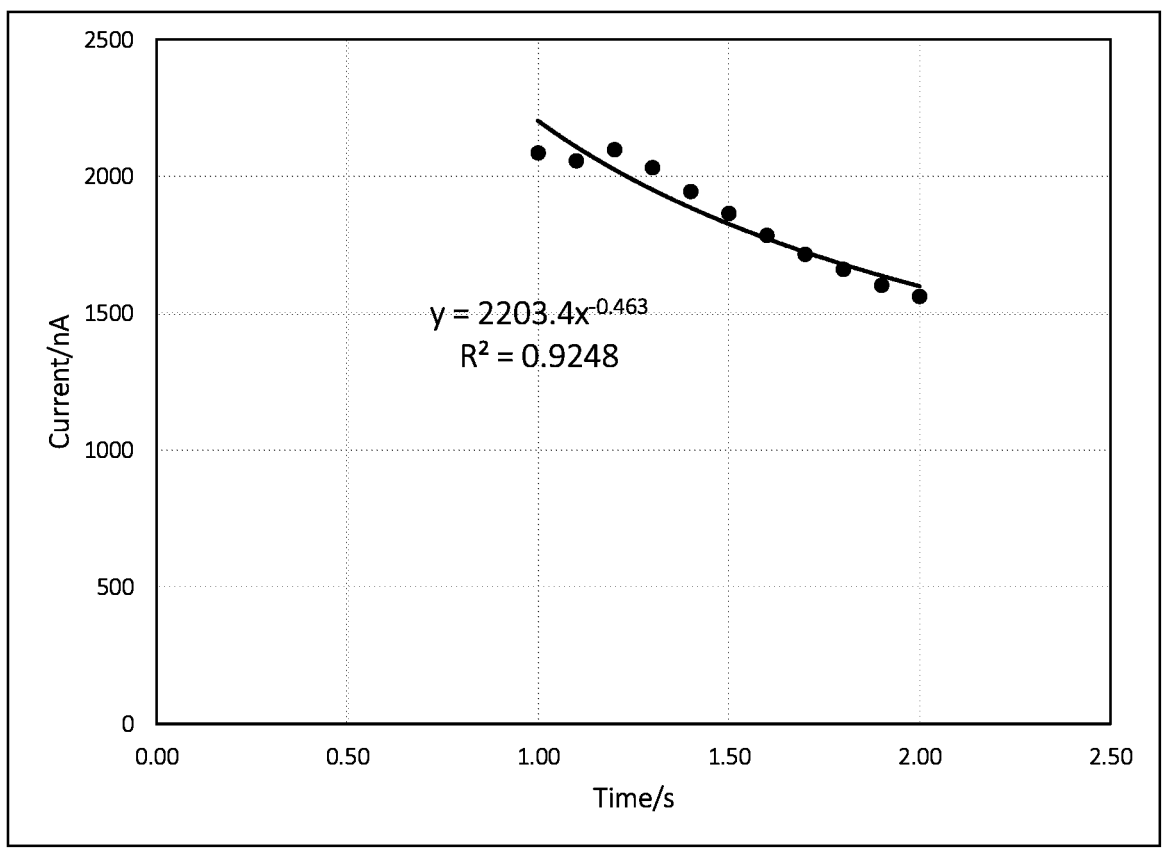
FIG. 4A is a current vs time (i-t) curve of abnormal background signal from 1 to 2 s. The equation and regression coefficient are derived from the data points of current vs time (1 to 2 s).
Figure 4B:
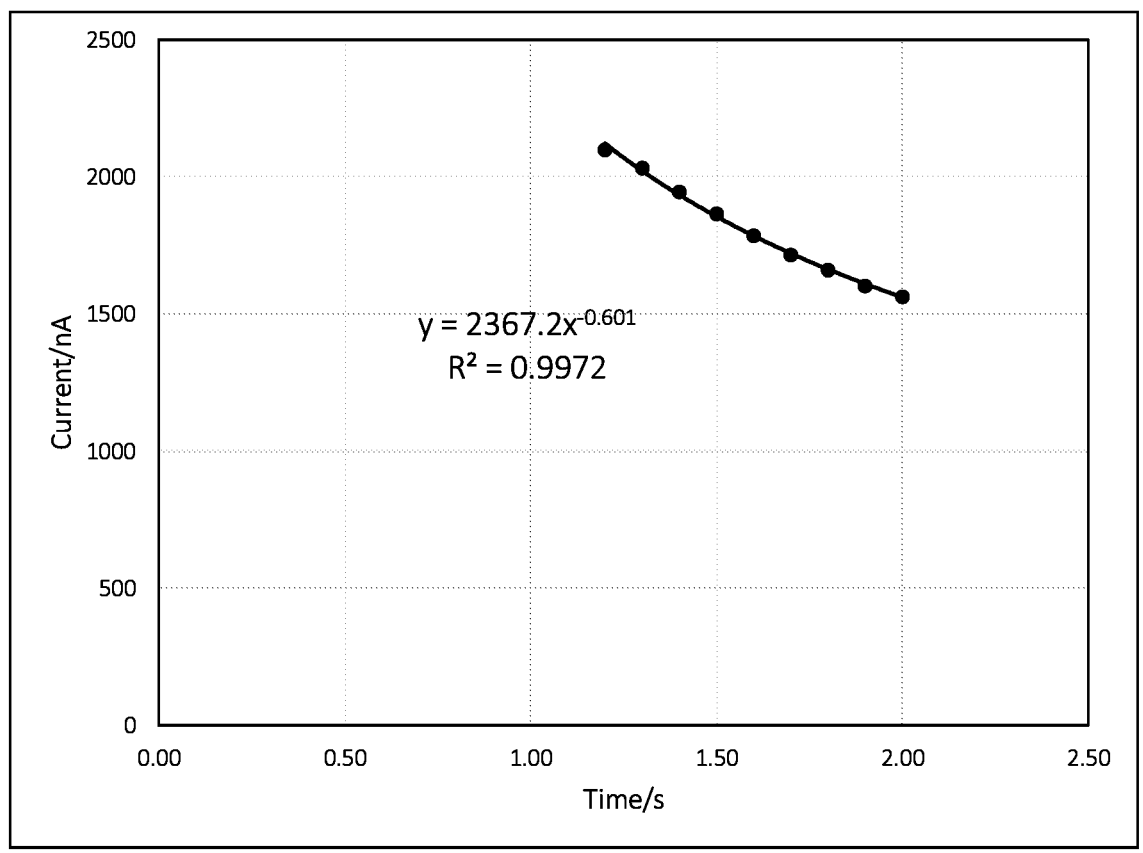
FIG. 4B is a current vs time (i-t) curve of the same background signal as FIG. 4A after removing abnormal data points. The equation and regression coefficient are derived from the remaining data points of current vs time (1.2 to 2 s).

It could happen that even after 1 s, the current may not decay as expected. A hump may appear for whatever reasons. FIG. 4A is a current vs time (i-t) curve of such abnormal background signal from 1 to 2 s. If a curve-fitting is also done from 1 to 2 s, and the resulting curve-fitting equation and regression coefficient are obviously not so good, this can be seen from the fitted curve and the regression coefficient (0.9248). To avoid this happening, more data points should be ruled out from curve-fitting. FIG. 4B is a current vs time (i-t) curve of the same background signal as FIG. 4A after removing two abnormal data points (time point 1, and 1.1 s). The equation and regression coefficient are derived from the remaining data points of current vs time (1.2 to 2 s). It is obvious that after removing the abnormal data points, a much better curve-fitting is achieved (0.9972 regression coefficient). Figuring out abnormal data points and ensuing curve-fitting can be conducted automatically by the meter using existing software skills and will not be further discussed in here.

Figure 5:
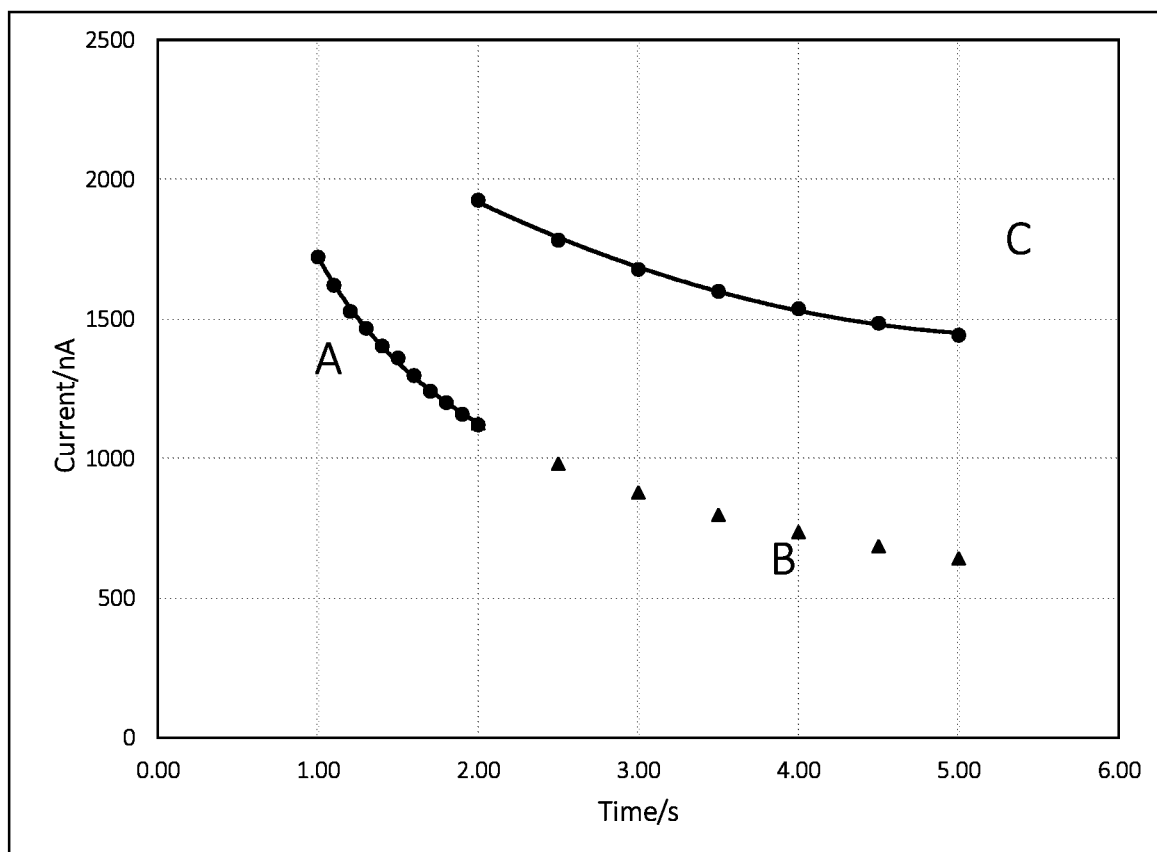
FIG. 5 are current vs time (i-t) curves: A, recorded background signals from 1 to 2 s; B, extrapolated background signals from 2 to 5 s using curve-fitting equation resulted from the curve A; C, recorded current signals at the working electrode from 2 to 5 s.

To illustrate background current subtraction from the working current, a background current, calculated or extrapolated background current, as well as working current are integrated in one figure. FIG. 5 are current vs time (i-t) curves: A, recorded background signals from 1 to 2 s; B, extrapolated background signals from 2 to 5 s using curve-fitting equation resulted from the curve A; C, recorded current signals at the working electrode from 2 to 5 s. The procedure of the background current subtraction is as below:
Step 1: Apply a potential for the blank electrode (without loading an enzyme) against the other electrode, record current for the first 2 s;
Step 2, Pause for 0.1 s (i.e., the electrodes are disconnected);
Step 3: Apply a potential for the working electrode (with loading an enzyme) against the other electrode, record current for the last 3 s;
Step 4: Run curve-fitting using data from step 1 and obtain curve-fitting equation and calculate current at 5 s using the equation;
Step 5: Subtract the background current from the working electrode current at 5 s, thus obtain the current signal representing the analyte concentration.
All the above steps can be programmed and performed automatically by the meter.

To verify the potential reverse and curve-fitting technology for the background correction using the test sensor and meter with the background correction software of the present invention, several interferents of clinical importance, including acetaminophen, methyldopa, vitamin C, glutathione, L-Dopa, bilirubin and uric acid were tested. For comparison, meters without the background correction software were also used for testing. Fresh venous blood samples were spiked with the interferents at their clinically important concentration and were tested along with un-spiked blood samples. FIGS. 6 and 7 summarize the test results with and without using the potential reverse and curve-fitting technology for the background correction, respectively. It appears that all the interferents, except vitamin C and bilirubin at high glucose concentrations, show serious interference with the measurement of glucose (>10% bias) without using the potential reverse and curve-fitting technology. However, the test results are all within 10% bias with using the potential reverse and curve-fitting technology described above showing remarkable advantage.

There is no doubt that the fluid chamber with two electrodes can be shorter than that with three electrodes and, as a result, the chamber volume is significantly reduced. This potential reverse and curve-fitting technology enable the test sensor having a shorter fluid chamber with two electrodes only to function as three electrodes (i.e., one blank electrode, one reference electrode and one working electrode) without compromise of the sensor performance.

It should be noted that although the particular embodiments of the present invention have been described herein, the above description is merely for illustration purpose. Further modification and variations of the invention herein disclosed will occur to those skilled in the respective arts and all such modifications and variations are deemed to be within the scope of the invention as defined by the appended claims.

What is claimed is:

1. An electrochemical test system comprising:
an electrochemical test strip capable of receiving a fluid in a fluid chamber and comprising a first electrode and a second electrode within the fluid chamber; and
a meter, the electrochemical test strip in electronic communication with the meter, wherein the meter is programmed to:
apply a first potential to the first electrode against the second electrode for a first time period;
measure a measured background current caused by the applied first potential to the first electrode against the second electrode during the first time period;
apply a second potential to the second electrode against the first electrode for a second time period, wherein the first time period occurs before the second time period;
measure a working current caused by the applied second potential to the second electrode against the first electrode during the second time period;
extrapolate an extrapolated background current for the second time period based on the measured background current during the first time period; and
calculate a difference between the extrapolated background current at a time during the second time period and the working current at the time during the second time period, the calculated difference being a current signal representing an analyte concentration.

2. The electrochemical test system of claim 1 wherein the electrochemical test strip comprises only two electrodes.

3. The electrochemical test system of claim 1 wherein the meter is programmed to extrapolate the extrapolated background current using curve-fitting.

4. The electrochemical test system of claim 3 wherein the curve-fitting begins using measurements starting approximately 0.5-1 second after the meter applies the first potential.

5. The electrochemical test system of claim 1 wherein the first electrode of the electrochemical test strip is positioned adjacent to an opening of the fluid chamber, and the second electrode is positioned at an opposite end of the fluid chamber from the first electrode.

6. The electrochemical test system of claim 1 wherein the second electrode of the electrochemical test strip is positioned adjacent to an opening of the fluid chamber, and the first electrode is positioned at an opposite end of the fluid chamber from the second electrode.

7. The electrochemical test system of claim 1 wherein the first time period is approximately two seconds.

8. The electrochemical test system of claim 7 wherein the second time period is approximately three seconds.

9. The electrochemical test system of claim 1 wherein the first electrode comprises a first chemistry, and wherein the second electrode comprises a second chemistry which comprises the first chemistry with an enzyme.

10. The electrochemical test system of claim 1 wherein the time during the second time period is at an end of the second time period.

11. The electrochemical test system of claim 1 wherein the meter is programmed to stop applying any potential between applying the first potential and applying the second potential.

12. A method of measuring an analyte concentration comprising:
    applying a first potential to a first electrode of an electrochemical test strip against a second electrode of the electrochemical test strip for a first time period by a meter in electronic communication with the electrochemical test strip;
    measuring a measured background current caused by applying the first potential during the first time period by the meter;
    applying a second potential to the second electrode against the first electrode for a second time period by the meter, wherein the first time period occurs before the second time period;
    measuring a working current caused by applying the second potential during the second time period by the meter;
    extrapolating, by the meter, an extrapolated background current for the second time period based on the measured background current during the first time period; and
    calculating a difference between the extrapolated background current at a time during the second time period and the working current at the time during the second time period, the difference being a current signal representing the analyte concentration.

13. The method of claim 12 wherein the electrochemical test strip comprises only two electrodes.

14. The method of claim 12 wherein the first electrode comprises a first chemistry, and wherein the second electrode comprises a second chemistry which comprises the first chemistry with of an enzyme.

15. The method of claim 12 further comprising a step of stopping any application of potential between the first electrode and the second electrode between the first time period and the second time period.

16. The method of claim 12 wherein the extrapolating of the extrapolated background current comprises using a curve-fitting.

17. The method of claim 16 wherein the curve-fitting begins using measurements starting after 0.5-1 second after the meter applies the first potential.

* * * * *